(12) United States Patent
Petit et al.

(10) Patent No.: US 7,838,695 B2
(45) Date of Patent: Nov. 23, 2010

(54) NEUROACTIVE SUBSTANCE AND USES OF ONE SUCH SUBSTANCE

(75) Inventors: Karina-Ethel Petit, Nantes (FR); Jean-Francois Biard, Nantes (FR); Bruno Lapied, Nantes (FR); Francoise Grolleau, Avrille (FR); Alain Hamon, Angers (FR)

(73) Assignee: Universite de Nantes, Nantes (FR)

( * ) Notice: Subject to any disclaimer, the term of this patent is extended or adjusted under 35 U.S.C. 154(b) by 803 days.

(21) Appl. No.: 10/581,226

(22) PCT Filed: Nov. 25, 2004

(86) PCT No.: PCT/FR2004/003030

§ 371 (c)(1),
(2), (4) Date: Feb. 26, 2007

(87) PCT Pub. No.: WO2005/056000

PCT Pub. Date: Jun. 23, 2005

(65) Prior Publication Data

US 2007/0161703 A1    Jul. 12, 2007

(30) Foreign Application Priority Data

Dec. 2, 2003    (FR) .................................. 03 14167

(51) Int. Cl.
*C07D 303/00*    (2006.01)
*A01N 43/20*    (2006.01)

(52) U.S. Cl. ....................................... 549/545; 514/475
(58) Field of Classification Search ................. 549/545; 514/475
See application file for complete search history.

(56) References Cited

OTHER PUBLICATIONS

L.A. Morris et al.: "A bioactive secosterol with an unusual A- and B-ring oxygenation pattern isolated from an Indonesian soft coral-Lobophytum sp.", Journal of Natural Products, 1998, vol. 61, No. 4, pp. 538-541.
D. Green et al.: "Secondary metabolites of the yellow and gray morphs of the soft coral *Parerythropodium fulvum fulvum*: Comparative aspects", Journal of Natural Products (Lloydia), 1992, vol. 55, No. 9, pp. 1186-1196.
S. Naz et al., "New antiproliferative epoxysecosterols from *Pseudopterogorgia americana*", Tetrahedron Letters, 2000, vol. 41, No. 32, pp. 6035-6040.

*Primary Examiner*—Janet L Andres
*Assistant Examiner*—David E. Gallis
(74) *Attorney, Agent, or Firm*—Z. Peter Sawicki; Westman, Champlin & Kelly, P.A.

(57) ABSTRACT

The invention relates to a neuroactive substance which is characterised in that it has formula (O), wherein R1, R2, R3 and R4 are identical or different and are methyl or ethyl radicals. Preferably, the neuroactive substance comprises 6S-acetyl-4R,5R-dimethyl-1R(10S)-epoxy-2R-hy-droxy-7R-acetoxydecahydro naphthalene which can be isolated from *Rhytisma fulvum* cnidaria. The inventive neuroactive substance can be used as a pharmacological reagent in research work and is also suitable for use in the fields of industry (insecticides) and health.

16 Claims, 2 Drawing Sheets

NEUROACTIVE SUBSTANCE AND USES OF ONE SUCH SUBSTANCE

CROSS-REFERENCE TO RELATED APPLICATION

Figure 1:
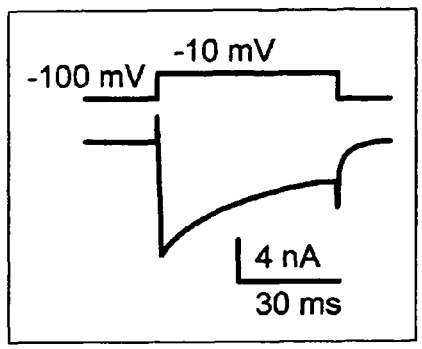

This Application is a Section 371 National Stage Application of International Application No. PCT/FR04/03030, filed 25 Nov. 2004 and published as WO 2005/056000 on 23 Jun. 2005, not in English, which is based on French application No. FR 03 14167, filed Dec. 2, 2003.

The invention essentially relates to the field of biochemistry.

More specifically, the invention relates to the field of neuroactive substances.

Cells are delimited by membranes displaying selective permeabilities for several ions, essentially $Na^+$, $K^+$, $Ca^{2+}$ and $Cl^-$ ions.

These selective permeabilities are provided by ion channels which consist of transmembrane proteins forming pores through the cell membranes.

These pores allow passive ion transmembrane flows and thus play predominant roles in numerous cell functions such as excitation, synaptic transmission, secretion or contraction.

The ion flows through the membrane are subject to an electrochemical force determined both by asymmetric distribution of each of the ions on either side of the membrane, i.e. a concentration gradient, and by an electric field, according to the Nernst equation.

If all ion species are taken into consideration, the system evolves towards a state of equilibrium which defines the potential of the cell at rest. According to the cell type, this potential varies between −40 mV and −90 mV.

Therefore, ion channels have a primordial role in the cell function and many applications are expected for active products thereon.

Such neuroactive substances acting on ion channels are of particular interest for fundamental research, as when they are used as pharmacological agents, they provide more knowledge of nerve function mechanisms.

In parallel, it is known that a number of diseases or syndromes are associated with neuronal excitability disorders. Such neuroactive substances acting on ion channels may therefore also assist with the development of new medicinal products.

In this way, numerous fields associated with a disturbance of the central nervous system are currently being explored: neuropathic pain (spontaneous or associated with operations, cancer, shingles, etc., neurodegenerative disease (Alzheimer's disease, Parkinson's disease), psychological (schizophrenia) or neurological (epilepsy) disorders.

Therefore, there is a need for new neuroactive substances, particularly for those liable to act on ion channels.

For some fifty years, bioactive metabolite research has focussed on the marine world. In fact, due to their incredible biodiversity, oceanic species represent a vast reservoir of natural substances.

For example, with respect to neuroactive substances, omegaconotoxin has been isolated from a mollusc (*Conus magus*). This substance, which blocks some calcium channels, displays an efficacy 100 to 1000 greater than that of morphine. It is now used to produce a medicinal product intended to treat pain: ziconotide™.

Therefore, one aim of the present invention is to propose a new neuroactive substance acting on membrane ion channels.

In particular, one aim of the present invention is to propose such a substance liable to act on a type of calcium channel.

Another aim of the present invention is to propose such a substance displaying potential for the production of medicinal products intended to treat neuronal excitability disorders (channel disease).

Another aim of the present invention is to present such a neuroactive substance which could, if applicable, be used as an insecticide, or antagonist, in humans, of the toxic effects of some insecticides.

These different aims are fulfilled by means of the invention which relates to a neuroactive substance characterised in that it complies with the formula (O)

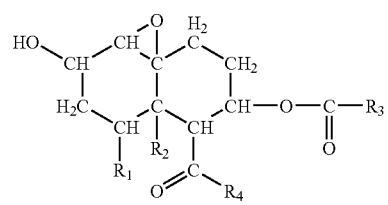

wherein R1, R2, R3 and R4 are identical or different and are methyl or ethyl radicals.

Preferentially, said substance complies with the formula (I)

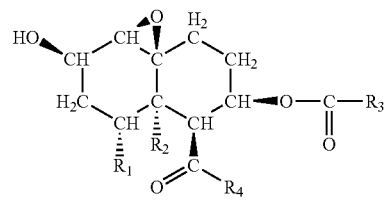

which displays a specific stereochemistry with respect to formula (O)

Most preferentially, this substance consists of 6S-acetyl-4R,5R-dimethyl-1R(10S)-epoxy-2R-hydroxy-7R-acetoxy-decahydronaphthalene according to formula (II)

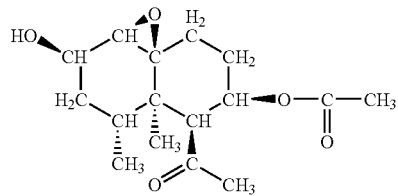

Such a substance complies with formula (I) specified above where R1, R2, R3 and R4 each consist of a methyl radical.

This substance was isolated by the inventors in a coral, i.e. the Cnidarian *Rhytisma fulvum*.

The *Rhytisma fulvum* species belongs to the Alcyoniidae family, the Alcyonacea order, the Octocorallia subclass, the Anthozoa class, and the Cnidaria phylum. This *Cnidarian* species was described by Forskal in 1775 and by Alderslade in 2000 (Zool. Med. Leiden, 2000, 74(16): 237-249).

*Rhytisma fulvum* is a coral which displays a wide bathymetric distribution as it ranges from −3 m to −40 m. Its geographic distribution locates it in tropical seas on occasional sites, but in particular abundance. It is found particularly in the Red Sea, Zanzibar, Madagascar, the Paternoster Islands (Indonesia), New Guinea and along the Australian Great Barrier Reef.

Numerous metabolites have already been isolated from *Rhytisma fulvum* particularly by Bowden et al. Tetrahedron Lett., 1980, 21 (32): 3105-3108, by Green et al. J. Nat. Prod., 1992, 55 (9): 1186-1196 and Wessels et al, J. Nat. Prod., 2001, 64 (3): 370-372. No pharmacological activity has been associated with them.

All these metabolites belong to the terpene chemical class. To the Applicant's knowledge, the metabolite according to formula (II) has never been described.

As will be explained below in more detail, the inventors proved that this substance according to formula (II) displayed neuroactivity in the cockroach. More specifically, the researchers proved that this substance according to formula (II) was a specific activator of transient low voltage activated calcium channels, which, to their knowledge, makes it the first membrane activator of this type of calcium channel.

Therefore, this substance (II) could be used in fundamental research as a pharmacological reagent particularly within the scope of work involving membrane ion channels.

At the present time, the researchers have not yet determined whether this neuroactivity was specific for insects or also existed in mammals, or in humans.

If the neuroactivity of this substance subsequently proves to be specific for insects, this substance may possibly to be used to produce insecticides. Within this scope, this substance may be used alone or in combination with at least one other insecticide particularly such as those inducing a neuroactivity opposing that of the compound according to the invention.

If, on the other hand, the neuroactivity of this substance is also observed in humans, this substance may be used to

- produce dopaminergic neuron activator medicinal products, for example, liable to be used in particular to treat Parkinson's disease which is characterised among other things by a decrease in the action potential frequency of this type of neuron;
- produce medicinal products intended to treat the decrease in the action potential frequency of pacemaker activity neurons. This production may be extended to use in the treatment of heart disorders.

It should be noted that the substance according to formula (II) isolated by the inventors in *Rhytisma fulvum* may be synthesised chemically. Within this scope, substances according to formula (I) may be obtained wherein the radicals R1, R2, R3, R4 will consist of methyl and/or ethyl radicals. The inventors consider that the substances according to formula (O) or formula (I), similar to the substance according to formula (II), are also liable to display neuroactivity and therefore be used for the same applications as those mentioned above.

Figure 2:
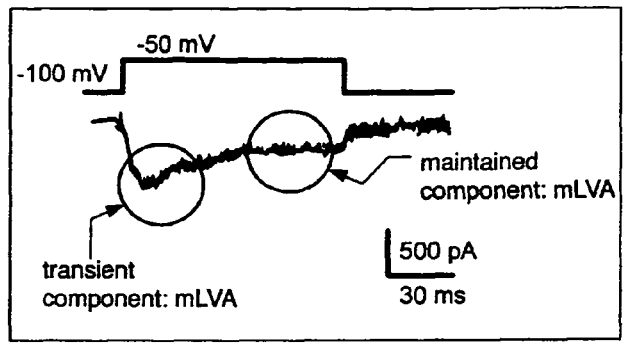
Figure 3:
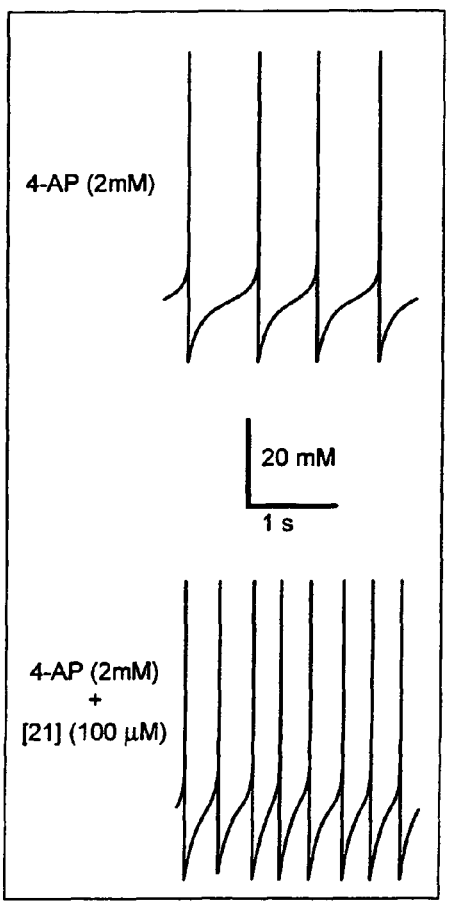
Figure 4:
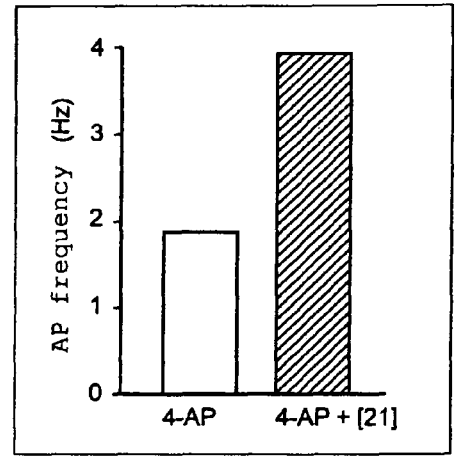
Figure 5:
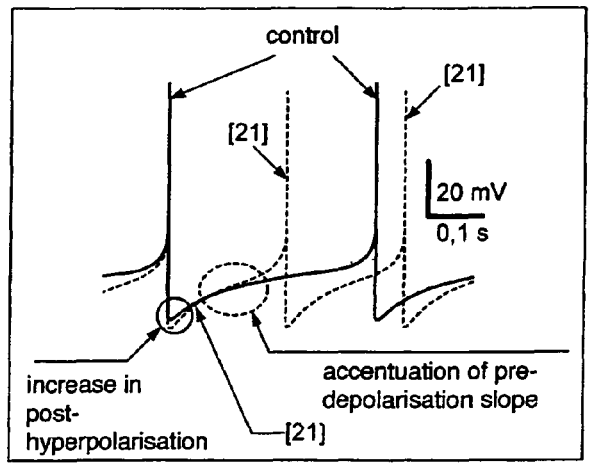
Figure 6:
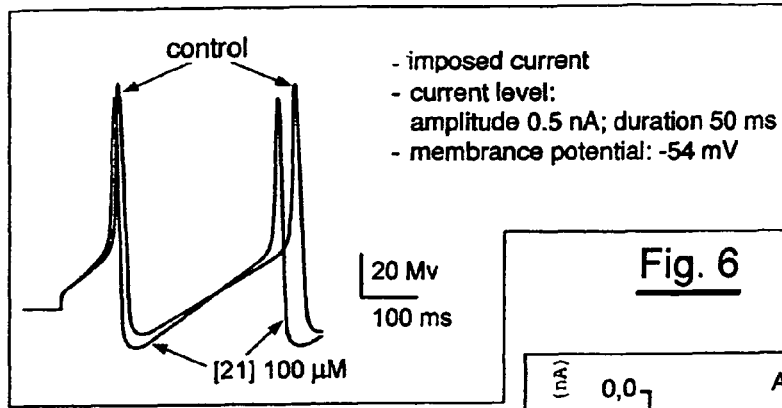
Figure 7:
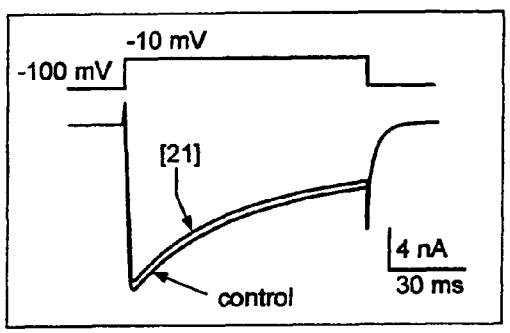
Figure 8:
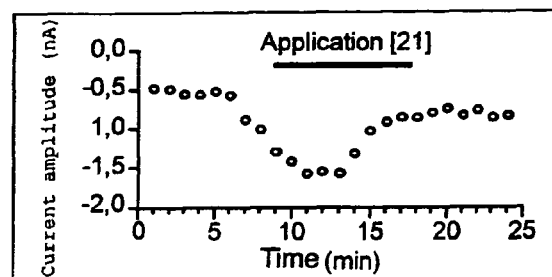
Figure 9:
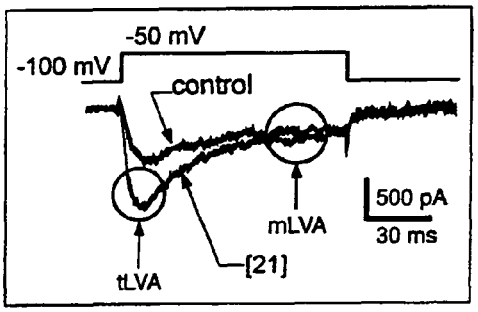
Figure 10:
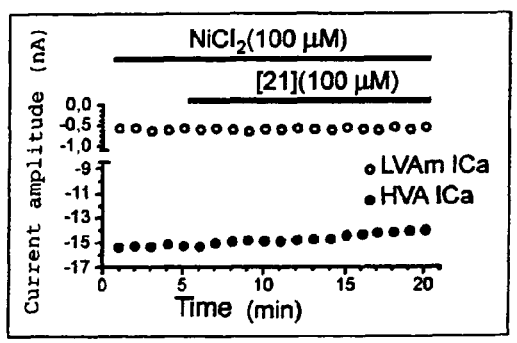
Figure 11:
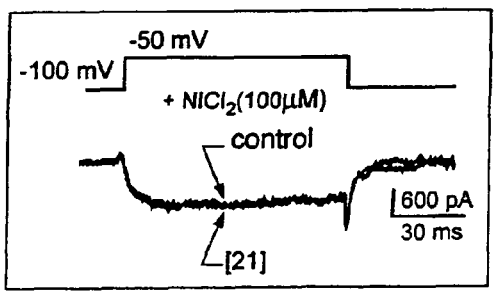
Figure 12:
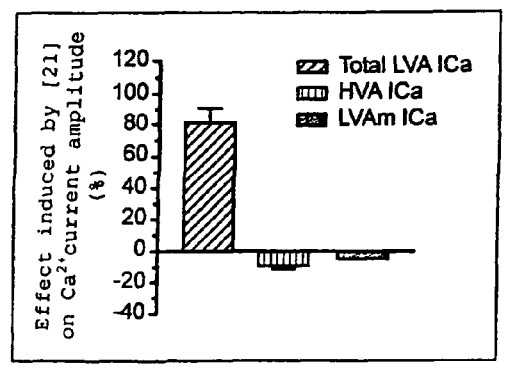

The invention, and the various advantages it offers, will be understood more easily by means of the following description of the work conducted by the inventors demonstrating neuroactivity in the cockroach (*Periplaneta americana*) of the substance according to formula (II). This description is given with reference to the figures wherein:

FIGS. 1 and 2 relate to the three types of calcium currents;

FIGS. 3, 4 and 5 relate to the effect of the substance according to formula (II) of the spontaneous electrical activity of cockroach DUM neurons;

FIG. 6 relates to the influence of the substance according to formula (II) of the action potentials activated on cockroach DUM neurons;

FIG. 7 relates to the effect of the substance according to formula (II) on the HVA calcium current in the case of a depolarising pulse;

FIG. 8 relates to the effect of the substance according to formula (II) on the amplitude of the overall LVA calcium current depending on time;

FIG. 9 relates to the effect of the substance according to formula (II) on the amplitude of the overall LVA calcium current in response to a depolarising pulse;

FIG. 10 relates to the effect of the substance according to formula (II) in the presence of nickel chloride on the amplitude of the mLVA and HVA calcium current;

FIG. 11 relates to the effect of the substance according to formula (II) in the presence of nickel chloride on the amplitude of the mLVA calcium current recorded in the case of a depolarising pulse;

FIG. 12 summarises the effects of the substance according to formula (II) on the amplitude of the different calcium currents.

2625 g of *Rhytisma fulvum* coral was caught in the seas off Djibouti was used to obtain a 33.5 g ethanol extract (yield 1.28%).

The substance according to formula (II) was extracted by means of a conventional chromatography process according to the procedure described below.

The *Rhytisma fulvum* ethanol extract underwent Vacuum Liquid Chromatography (VLC) on silica. Elution was performed with a mixture of dichloromethane ($CH_2Cl_2$) and methanol (MeOH).

Vacuum Liquid Chromatography with a non-polar $C_{18}$ stationary phase was then performed on 98:2 $CH_2Cl_2$/MeOH fraction obtained in the previous step with an eluent consisting of a mixture of methanol (MeOH) and water.

Vacuum Liquid Chromatography on silica was then performed on the 50:50 MeOH/$H_2O$ fraction obtained in the previous step with an eluent consisting of hexane and acetone.

High performance Liquid Chromatography on silica gel (Nucleosil® 5μ mSi) was then performed on the 60/40 hexane/acetone fraction obtained in the previous step with an eluent consisting of dichloromethane and ethanol (EtOH).

The fraction displaying a retention time between 7 min 30 and 9 min then underwent High Performance Liquid Chromatography on silica gel (Nucleosil® 5μ mSi) using an eluent consisting of dichloromethane and ethanol (EtOH) which made it possible to obtain two fractions one of which displayed a retention time between 25 and 34 minutes. This fraction was analysed and indicated that it was a compound according to formula (II).

During these experiments, the chromatographic equipment used for the Vacuum Liquid Chromatography displayed the following characteristics:

adsorbent: 60 Å silica, grain size 35-70 μm, Chromagel SDS; C18, 60 Å, grain size 60 μm, Macherey-Nagel glass column with glass wool as filter.

The chromatographic equipment used for High Performance Liquid Chromatography displayed the following characteristics:

pressure gauge: 806 manometric module, Gilson solvent pump: 305 pump, Gilson injector: Rheodyne valve, 100 μl loop detectors: 115 UV and 132 RI, Gilson Printer: SE120, BBC Guerz Metrawatt analytical columns: 250×4.6 mm, Nucleosil 5 μm Si preparatory column: 250×22 mm, Rsil 10 μm syringe: 100 μl or 500 μl, Hamilton.

It should be noted that the substance according to formula (II) was obtained with a 1.05% yield with reference to the initial ethanol extract, i.e. 0.0013% by weight with reference to the raw material.

The neuroactivity of the substance according to formula (I) was then tested by injecting in Diptera larvae. Within this scope, the inventors used *Phormia terrae novae* species Cyloraphe larvae at larval stage III, just before the imago stage enabling metamorphosis to a pupa or nymph. This type of larvae is available in fishing shops and is stored in bran at 4° C. for not more than 10 days.

The product is injected using a precision micro-syringe fitted with a bevelled hypodermic needle. The needle is inserted into the last abdominal segment of the animal on the dorsal side. The injection is deemed successful if the larva is still mobile at the tip of the needle. In this type of test, contraction or relaxation for at least 5 seconds is defined as a positive response, but the intensity and duration are dose-dependent while the absence of any symptom for 10 min represents a negative response.

Substance (II) was tested by injecting a single 350 μg dose of product per larva (mean larva weight 70 mg), by injecting 7 Al of a 50 mg/ml solution of the product in the 85-15 v/v water:DMSO mixture.

This concentration was then diluted by half until no larval activity was detected.

These tests made it possible to establish that the minimum active concentration on diptera larvae of the substance according to formula (II) is 3.1 μg per μl and per 10 mg of larvae.

As the molecular weight of the substance according to formula (II) is 296 g per mole, the MAC thereof is therefore approximately 1 mM/mg of larvae.

The inventors then studied the possible effects of the substance according to formula (II) on neuronal membrane ion currents.

Firstly, the neuronal sodium and potassium channels were studied. These channels are involved in action potential generation.

This study was conducted on cockroach (*Periplaneta americana*) giant axons. The giant axon of these cockroaches was isolated in ventral abdominal nerve chain connective tissue.

During the experiment, the axon is immersed in physiological fluid. The experiment is performed under imposed potential and imposed current in the absence and presence of the substance according to formula (II).

This experiment did not demonstrate any change on the action potential. Therefore, the substance according to formula (II) has no activity on axonal cockroach sodium and potassium channels.

A second experiment was conducted on dorsal unpaired median neurons (DUM neurons) from the central nervous system of cockroaches (*Periplaneta americana*). In particular, these neurons secrete a biogenous amine, octopamine, a neuromediator wherein the chemical structure is similar to dopamine in vertebrates. They represent a good study model as they display electrophysiological properties similar to those of dopaminergic neurons in vertebrates.

These DUM neurons are isolated from the medio-dorsal line of the last terminal abdominal ganglion of the nerve chain of adult male cockroaches, by means of enzyme digestion and mechanical dissociation, according to the technique described by Lapied et al (J. Exp. Biol., 1989, 144; 535-549). The neurons isolated in this way are kept in culture at 29° C. for 24 hrs before testing. The whole cell configuration patch-clamp technique is used to measure the electrical activity and the calcium currents (imposed potential and/or current conditions) according to the model described by Grolleau and Lapied (J. Neurophysiol. 1995, 73; 160-171).

The purpose of such an experiment is to determine the type of calcium channel on which the substance according to formula (II) acted.

In fact, there are two major groups of calcium channels, i.e. high voltage activated calcium channels (HVA—see FIG. 1) and low voltage activated calcium channels (LVA—see FIG. 2). Among the low voltage activated calcium channels, a distinction is made between transient LVA calcium channels (tLVA) and maintained LVA calcium channels (mLVA).

HVA calcium currents are activated for potentials close to −30 mV.

LVA calcium currents are activated for more negative potentials between −70 and −50 mV.

The transient LVA calcium current is characterised by an activation threshold at −70 mV. Inactivation is potential-dependent and independent from the $Ca^{2+}$ influx. This current, which is sensitive to nickel chloride (100 μM), is involved in the initial pre-depolarisation phase. It corresponds to the conventional type T current in vertebrates.

Maintained LVA calcium current is distinguished by an activation threshold at −60 mV, inactivation dependent on potential and the intracellular $Ca^{2+}$ concentration. It is insensitive to nickel chloride (100 μm) and is involved in the final pre-depolarisation phase.

A first series of experiments on DUM neurons demonstrated an effect of the substance according to formula (II) on "pacemaker" electrical activity. The experiments were conducted in the presence of 4-aminopyridine (4-AP, 2 mM) in order to block the type A potassium current, which is normally involved in maintaining a low action potential discharge frequency (Grolleau and Lapied, 1995). In the absence of 4-AP, activation of this current is liable to mask a potential variation of the action potential discharge frequency.

As demonstrated in FIG. 3 below, the action potential frequency is affected, but the amplitude remains unchanged. In the presence of substance (II) at 100 μm, the frequency is increased by a factor of 2.1 which is statistically significant as demonstrated in FIG. 4. The post-hyperpolarisation phase is also increased as demonstrated in FIG. 5. Finally, the pre-depolarisation slope is higher, which results in an earlier activation of the action potential, without any change in its duration or its amplitude.

Experiments were also conducted on an electrical activity activated by injecting a level of depolarising current controlled in amplitude and duration (FIG. 6). The results obtained under these conditions are in agreement with the experiments conducted on spontaneous activity. An increase both in the post-hyperpolarisation phase and the pre-depolarisation slope is observed. This is conveyed by an increase in the discharge frequency, as the action potential activation threshold is reached earlier. No change to the action potential amplitude or duration was observed.

All these observations tend to exclude a direct effect of the substance according to formula (II) on sodium and potassium channels as neither the action potential amplitude or duration are affected by its presence. Therefore, these observations confirm the results previously obtained on the giant cockroach axon. However, the substance according to formula (II) increases the action potential discharge frequency. However, they essentially consist of transient and maintained LVA type calcium currents, which are involved in the pre-depolarisation phase.

Both groups of calcium currents (i.e. HVA and LVA) are sufficiently different to be able to study the action of neuroactive compounds on each separately. Using an experimental protocol used to apply two depolarising pulses of different amplitudes, it is possible to record only the HVA current (test at −10 mV using a −100 mV reference potential) or the overall LVA current (test at −50 mV using a −100 mV reference potential). In the latter case, it is also possible to record only the mLVA current by working in the presence of 100 μM of nickel chloride. Under these conditions, the tLVA current is obtained by "subtracting" the overall LVA current with the mLVA. In all cases, the recordings are obtained in the presence of specific sodium and potassium current inhibitors (100 μM of tetrodotoxin, 100 mM of TEA-Cl and 5 mM of 4-AP, respectively).

When a +90 mV depolarising pulse is applied to the −100 mV reference potential, only the HVA calcium current is activated. However, the amplitude of this current is only reduced by 9% (n=7) with respect to the test in the presence of the substance according to formula (II). This variation is not significant and indicates that the product has very little action on the HVA type calcium current (FIG. 7).

When the substance according to formula (II) is applied to DUM neurons, the amplitude of the overall LVA calcium current, recorded in response to a +50 mV depolarising pulse using a −100 mV reference potential, increases immediately (+81%+24; n=7; FIG. 8). However, it clearly appears that the maintained component measured at the end of the depolarising pulse is not affected (FIG. 9). Therefore, these two experiments indicate that the substance according to formula (II) affects one of the two types of LVA calcium channels selectively. This hypothesis was verified by repeating the experiment, but this time in the presence of 100 μm of nickel chloride known to block the tLVA calcium current selectively.

The inventors observed that neither the amplitude of the mLVA current (FIGS. 10 and 11) or that of HVA are modified (FIG. 10). Therefore, this confirms that the substance according to formula (II) has a specific action on tLVA.

FIG. 12 summarises the effects of the substance according to formula (II) on the amplitude of the different calcium currents.

Therefore, the substance according to formula (II) increases the action potential discharge frequency by potentiating the tLVA type calcium channel. Therefore, the entry of calcium occurs and thus an accentuation of the pre-depolarisation slope which makes it possible to reach the action potential activation threshold more quickly.

The analogy between octopamine in insect DUM neurons and dopamine in the dopaminergic neurons in the black substance in the human brain may make it possible to envisage that a product that is active on the former may also be active on the latter.

If the substance according to formula (II) proves to be specific for insect calcium channels, this substance could be used in insecticides as specified above.

If, on the other hand, this substance also acts on tLVA calcium channels in vertebrates, it could be used to produce activator medicinal products, for dopaminergic neurons, for example, particularly to treat Parkinson's disease, and as medicinal products intended to treat diseases associated with a decrease in the action potential frequency of pacemaker activity neurons.

The invention claimed is:

1. An isolated neuroactive substance comprising the formula (0)

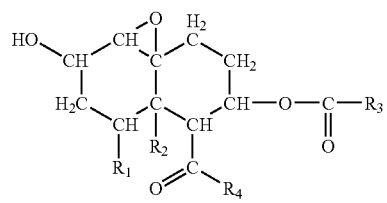

wherein R1, R2, R3 and R4 are methyl or ethyl radicals.

2. The neuroactive substance according to claim 1 comprising the formula (I)

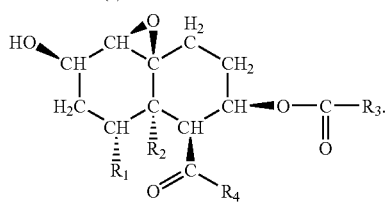

3. The neuroactive substance according to claim 2 comprising 6S-acetyl-4R,5R-dimethyl-1R(10S)-epoxy-2R-hydroxy-7R-acetoxydecahydronaphthalene according to formula (II)

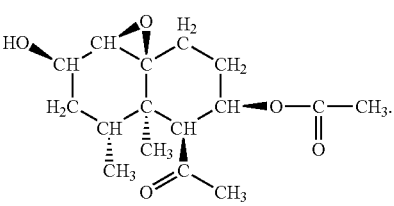

4. The neauroactive substance according to claim 3 characterised in that it is extracted from the Cnidarian *Rhytisma fulvum*.

5. A pharmacological reagent comprising the formula (0)

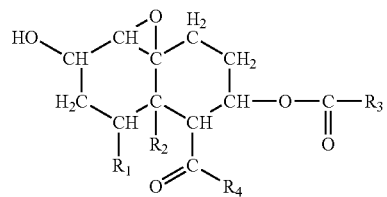

wherein R1, R2, R3 and R4 are methyl or ethyl radicals.

6. The pharmacological reagent according to claim 5 comprising the formula (I)

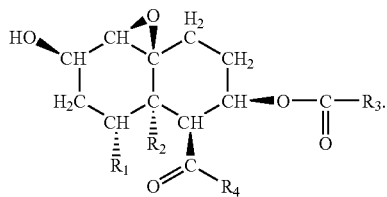

7. The pharmacological reagent according to claim 6 comprising 6S-acetyl-4R,5R-dimethyl-1R(10S)-epoxy-2R-hydroxy-7R-acetoxydecahydronaphthalene according to formula (II)

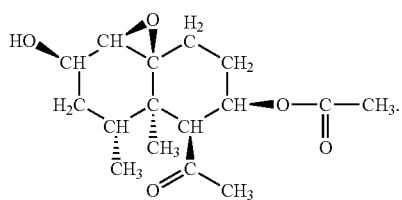

8. The pharmacological reagent of claim 5 comprising a selective transient low voltage activated calcium membrane channel activator.

9. The pharmacological reagent according to claim 5 comprising the formula (I).

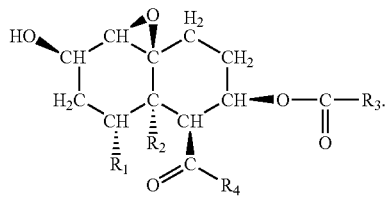

10. The pharmacological reagent according to claim 6 comprising 6S-acetyl-4R,5R-dimethyl-1R(10S)-epoxy-2R-hydroxy-7R-acetoxydecahydronaphthalene according to formula (II)

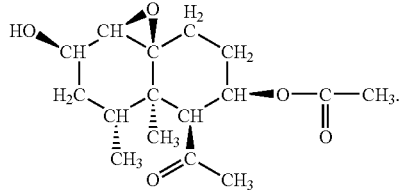

11. An insecticide comprising the formula (0)

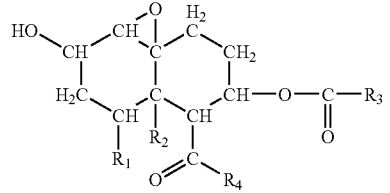

wherein R1, R2, R3 and R4 are methyl or ethyl radicals.

12. The insecticide according to claim 11 comprising the formula (I)

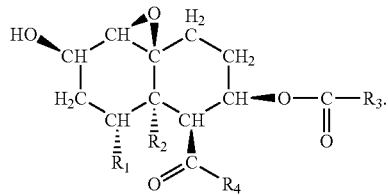

13. The insecticide according to claim 11 comprising 6S-acetyl-4R,5R-dimethyl-1R(10S)-epoxy-2R-hydroxy-7R-acetoxydecahydronaphthalene according to formula (II)

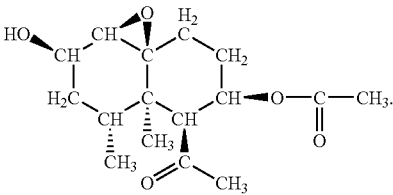

14. The insecticide of claim 11 and further comprising another different insecticide.

15. The insecticide according to claim 11 comprising the formula (I)

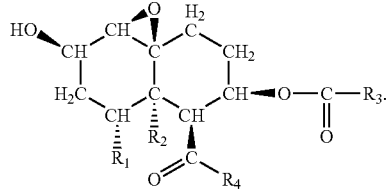

16. The insecticide according to claim 11 comprising 6S-acetyl-4R,5R-dimethyl-1R(10S)-epoxy-2R-hydroxy-7R-acetoxydecahydronaphthalene according to formula (II)

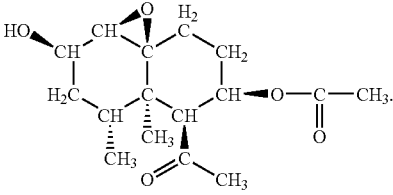

* * * * *